(12) United States Patent
Kallos et al.

(10) Patent No.: US 11,693,069 B2
(45) Date of Patent: Jul. 4, 2023

(54) TUNABLE METAMATERIAL DEVICE FOR CONCENTRATING MAGNETIC FIELD OF RF SIGNALS IN AN MRI SYSTEM

(71) Applicant: Medical Wireless Sensing Ltd, London (GB)

(72) Inventors: Efthymios Kallos, London (GB); Shimul Chandra Saha, London (GB)

(73) Assignee: MEDICAL WIRELESS SENSING LTD., London (GB)

( * ) Notice: Subject to any disclaimer, the term of this patent is extended or adjusted under 35 U.S.C. 154(b) by 83 days.

(21) Appl. No.: 17/265,384

(22) PCT Filed: Aug. 1, 2019

(86) PCT No.: PCT/EP2019/070838
§ 371 (c)(1),
(2) Date: Feb. 2, 2021

(87) PCT Pub. No.: WO2020/025776
PCT Pub. Date: Feb. 6, 2020

(65) Prior Publication Data
US 2021/0293914 A1    Sep. 23, 2021

(30) Foreign Application Priority Data
Aug. 3, 2018   (GB) .................... 1812703

(51) Int. Cl.
*G01R 33/36*       (2006.01)
*A61B 5/055*       (2006.01)
(Continued)

(52) U.S. Cl.
CPC .......... *G01R 33/3607* (2013.01); *A61B 5/055* (2013.01); *G01R 33/288* (2013.01); *G01R 33/3415* (2013.01)

(58) Field of Classification Search
CPC .............. G01R 33/3607; G01R 33/288; G01R 33/3415; G01R 33/5659; G01R 33/36;
(Continued)

(56) References Cited

U.S. PATENT DOCUMENTS

2007/0290688 A1    12/2007  Vaughan
2010/0013483 A1*   1/2010   Odintsov ......... G01R 33/34046
                                                                324/318
(Continued)

FOREIGN PATENT DOCUMENTS

JP    06-017703      3/1994
JP    2009148556     7/2009
(Continued)

OTHER PUBLICATIONS

International Preliminary Report on Patentability in International Appln. No. PCT/EP2019/070838, dated Feb. 9, 2021, 14 pages.
(Continued)

*Primary Examiner* — Walter L Lindsay, Jr.
*Assistant Examiner* — Frederick Wenderoth
(74) *Attorney, Agent, or Firm* — Fish & Richardson P.C.

(57) ABSTRACT

The present disclosure is directed to a device and a magnetic resonance system for concentrating a magnetic field of radio frequency signals, and methods for concentrating a magnetic field of as radio frequency signal in an object to be imaged.

20 Claims, 3 Drawing Sheets

(51) Int. Cl.
*G01R 33/28* (2006.01)
*G01R 33/3415* (2006.01)

(58) Field of Classification Search
CPC . A61B 5/055; H01Q 15/0066; H01Q 15/0086
See application file for complete search history.

(56) References Cited

U.S. PATENT DOCUMENTS

2013/0002253 A1  1/2013  Werner et al.
2018/0188339 A1* 7/2018  Slobozhanyuk .......................... G01R 33/34092

FOREIGN PATENT DOCUMENTS

| JP | 2018520777 | 8/2018 |
| WO | WO 2008/078284 | 7/2008 |
| WO | WO 2017/007365 | 1/2017 |
| WO | WO 2020/025776 | 2/2020 |

OTHER PUBLICATIONS

Lim et al., "Switch-Tuned Dual-Frequency Birdcage RF Coil for 13C and 1H Imaging", International Society for Magnetic Resonance in Medicine, Apr. 1, 2012, p. 4300.

Issa et al., "A Reconfigurable Capacitive Impedance Surface for 1.5T Magnetic Resonance Imaging Applications", Loughborough Antennas & Propagation Conference (LAPC 2017), Nov. 13, 2017, XP055627138, 4 pages.

Kaneko et al., "B1-control receive array coil (B-RAC) for reducing B1+ inhomogeneity in abdominal imaging at 3T-MRI", Journal of Magnetic Resonance, vol. 287, Dec. 14, 2017, pp. 23-32.

Merkle et al., "Transmit B1-field correction at 7T using actively tuned coupled inner elements", Magnetic Resonance in medicine, vol. 66, No. 3, Mar. 24, 2011, pp. 901-910.

Slobozhanyuk et al., "Enhancement of magnetic Resonance Imaging with Metasurfaces", Advanced Materials, vol. 28, No. 9, Jan. 11, 2016, pp. 1832-1838.

Lapine et al., "Colloquium: Nonlinear metamaterials", Reviews of modern Physics, vol. 86, No. 3, Sep. 1, 2014, pp. 1093-1123.

International Search Report and Written Opinion for International Application No. PCT/EP2019/070838 dated Oct. 15, 2019, 20 pages.

Great Britain Combined Search and Examination Report dated Mar. 23, 2020 for Great Britain Application No. GB1812703.5 filed Aug. 3, 2018, 10 pages.

Office Action in Japanese Application No. JP 2021-529523, dated Jan. 31, 2023, 6 pages (with English Translation).

* cited by examiner

TUNABLE METAMATERIAL DEVICE FOR CONCENTRATING MAGNETIC FIELD OF RF SIGNALS IN AN MRI SYSTEM

CROSS-REFERENCE TO RELATED APPLICATIONS

This application is a U.S. National Stage entry of International Patent Application no. PCT/EP2019/070838, filed Aug. 1, 2019, which claims the benefit of priority of United Kingdom Patent Application no. 1812703.5, filed Aug. 3, 2018.

FIELD

The present disclosure relates to devices and methods for concentrating the magnetic field of signals in a Magnetic Resonance (MR) system and MR systems including such devices or implementing such methods.

BACKGROUND

Magnetic Resonance Imaging (MRI) is the only method capable of measuring brain neural activity, detecting early cancerous cells, imaging nanoscale biological structures, controlling fluid dynamics and functional cardiovascular imaging. The demand for MRI scans is increasing steadily, resulting in longer waiting times due to a limited number of machines. Increasing demand for higher resolution imaging has led to the development of higher static magnetic field scanners (3T or higher), which are more expensive. As the need for higher quality images and the volume of MRI scans are steadily increasing over time, national health systems experience high pressure in their effort to reduce waiting lists within existing facilities, resources, and budget constraints. Therefore, improvements in MRI screening efficiency under these conditions are needed to advance of medical imaging and diagnostics.

PCT application published as WO2017007365 (12 Jan. 2017) describes a metamaterial device for improving the Signal-to-noise ratio (SNR) of Radio-Frequency (RF) signals and reducing Specific absorption rate (SAR) in an MRI system. The device, functioning as an electromagnetic field concentrator, produces local redistribution of radio-frequency fields close to the subject being examined. This is by virtue of the fact that the length of each conductor in the electromagnetic field concentrator satisfies the requirement for the emergence of half-wave resonance. This device is particularly suited for relatively low power MRI systems. Given the potential for significant concentration of electromagnetic (EM) fields offered by this device, there is a risk of RF signals being concentrated to an unacceptable level of SAR in high power systems. A further problem is that, when the object being imaged is inside an MRI system, the dielectric properties of the object may detune a transmit or receive coil of the MRI system. The amount of detuning varies depending on the particular properties of the object. This detuning means the coil will operate sub-optimally since the coils are detuned from the Larmor frequency.

SUMMARY

According to a first aspect herein, a device for concentrating a magnetic field of RF signals in an MR system comprises a plurality of conductive elements arranged in an array. The array of conductive elements is arranged to redistribute energy between electric and magnetic fields of RF radiation at a resonant RF frequency when receiving an RF signal having a RF wavelength greater than a respective dimension of each conductive element. The redistribution of energy may comprise increasing the local magnetic field strength of the RF signal at a first location of the array and decreasing the local electric field strength of the RF signal at the first location. This redistribution is effectively an 'concentration' of the magnetic field of the RF signal at the first location. Since the effect of the incoming RF signal pulse on the magnetic moments of atoms depends on the magnetic field strength, this redistribution improves the effect of the RF signal. Additionally, the reduction in electric field at the first location may reduce undesired heating of the subject to be imaged. Hence placing the subject to be imaged in proximity to the first location may improve the signal-to-noise ratio of the MR system, while also reducing the specific absorption ratio.

The redistribution of energy between electric and magnetic fields of RF radiation is dependent in part of the resonance of the conducting elements in the array at a resonant RF frequency, i.e. the redistribution is a phenomenon that occurs at the resonant frequency. When receiving an RF signal including this frequency, the conductive elements in the array resonate. The RF signal may be received from an RF transmitter before the RF signal reaches an object to be imaged, or the RF signal may be received from the object (i.e. a return RF signal) after the object has been irradiated. The RF signal has an RF wavelength greater than a respective dimension of each conductive element. In other words, the conducting elements are 'sub-wavelength' in size.

The device further comprises a plurality of semiconductor devices each connected between two respective portions of the conductive elements. The two respective portions may be two portions of a single respective conductive element. Alternatively, a first respective portion may be on a first respective conductive element and a second respective portion may be on a second respective conductive element. In other words, each semiconductor device may be connected to a single conductive element or connected to multiple conductive elements. The resonant frequency of the array depends on a conduction state and/or a capacitance of each semiconductor device, which are determined by a bias voltage of the semiconductor device. The conduction state indicates whether or not, or how much, the semiconductor device conducts electricity between the two portions. For example, the conduction state when the semiconductor device conducts between the two portions can be called "conducting", "ON", or "closed". Conversely, if the semiconductor device does not conduct between the two portions, the conduction state is "non-conducting", "OFF", or "open". In general, the semiconductor devices may not ever be perfectly insulating or perfectly conducting. However, the conducting/non-conducting conduction states substantially approximate a circuit short or a circuit break between the two portions. In particular, the 'non-conducting' state produces a resonant frequency substantially equal to the resonant frequency of the array if it had unconnected conductive elements. Likewise, the 'conducting' state produces a resonant frequency of the array substantially equal to the resonant frequency of the array if it had conductive elements connected by a conductor with negligible resistance. The bias voltage is a voltage which can be applied between two points of the semiconductor device to control electrical properties of the semiconductor device. For example, the bias voltage of a transistor is between the transistor gate and transistor source, whereas the bias voltage of a varactor diode is between the anode and cathode of the varactor diode. If the semiconductor is forward biased, the bias voltage determines a conduction state of the semiconductor device. Alternatively, if the semiconductor is reverse biased, the bias voltage determines a capacitance of the semiconductor device. Controlling either a conduction state or a capacitance between conductive elements will control the resonant frequency of the array of conductive elements.

The device further comprises a controller to control the bias voltage of each semiconductor device. In general, the controller may control the bias voltage of each respective semiconductor device independently or may control the bias voltages of all the semiconductor devices collectively. Since the resonant frequency depends on the bias voltage of the semiconductor devices (which provides the conduction state or capacitance of the semiconductor device), controlling the bias voltage can selectively change, i.e. 'tune' or 'de-tune', the resonant frequency. For example, the resonant frequency can be 'tuned' to match a frequency of the RF signal so that the device redistributes energy between electric and magnetic fields as described above. Alternatively, the resonant frequency can be 'de-tuned' from a frequency of the RF signal so that the device does not redistribute energy between electric and magnetic field as described above. For example, if RF signal doesn't comprise the 'de-tuned' resonant frequency (or at least its spectrum does not comprise a substantial proportion of that resonant frequency) it will not resonate.

Accordingly, a device according to the first aspect can advantageously control whether or not the RF signal magnetic field redistribution/concentration occurs. For example, the magnetic field redistribution/concentration phenomenon can be controlled to only occur during certain phases of an MR system RF pulse cycle.

The device may be arranged such that each of one or more of the plurality of semiconductor devices is coupled between a respective pair of the conductive elements, such that the conductive elements of the respective pair are shorted when the respective semiconductor device is conducting. For example, the two points of a semiconductor device connect a pair of conducting elements so that, when the semiconductor device is in the conduction state 'non-conducting', the pair are electrically isolated. Conversely, when the semiconductor device is in conduction state 'conducting', the pair are electrically connected or 'shorted'. The pair of conducting elements may be adjacent conducting elements in the array. Any individual conducting element may be in one or more pairs. For example, semiconductor devices may connect the conducting elements so that, when the plurality of semiconductor devices are 'conducting', all or most of the conductive elements are electrically connected.

The device may comprise one or more conductive element extensions each arranged in line with a respective conductive element, e.g. parallel to and colinear with the respective conductive element and arranged at one end of the respective conductive element. In this arrangement, each of one or more of the plurality of semiconductor devices is coupled between a respective conductive element and a corresponding conductive element extension. This extends an effective length of the respective conductive element when the respective semiconductor device is conducting. In general, the resonant frequency, and therefore the redistribution of energy effect, depends on the length or effective length of the conductive elements. Hence extending (or otherwise changing) the effect length of the conductive elements will tune/de-tune the device.

The conductive elements may each be elongate, that is having a first dimension (length) which is multiple times longer than its second and third dimensions. For example, the conductive elements may be wires. Each elongate conductive element has length of approximately half the wavelength of the resonant frequency, which produces a redistribution of energy between the electric and magnetic fields with a local increase in magnetic field (and a corresponding decrease in electric field) near the midpoint along the length of the conductive elements. The elongate conductive elements are arranged substantially parallel to each other, i.e. with the lengths of the conductive elements substantially parallel. For example, substantially parallel means sufficiently parallel such that the redistribution of energy phenomenon in each conductive element cooperates so that the device produces an imaging target region of locally increased magnetic field and decreased electric field. The conductive elements may be spaced from each other in a direction transverse to the length of the conductive elements.

The array may be one-dimensional (arranged side by side in a single row), two-dimensional (arranged in stacked layers of rows) or three-dimensional (in stacked layers of a two-dimensional array).

The conductive elements may comprise one or more curved elements, the one or more curved elements comprising one or more of a split ring, a loop, and a swiss roll, wherein a respective semiconductor device is coupled between ends of each of the one or more curved elements. Accordingly, when the semiconductor device is 'conducting', the ends of the curved elements are shorted thereby changing the resonant frequency.

The conductive elements may comprise a curved wire medium, wherein a respective semiconductor device is coupled between one or more pairs of adjacent wires of the curved wire medium. When a semiconductor device is 'conducting', the pair curved wires are shorted thereby changing the resonant frequency.

The controller may be arranged to modify the bias voltage of each semiconductor device in response to receiving the RF signal. For example, the controller may control the bias voltage so that the conduction state of each semiconductor device is 'conducting' when the controller determines that an RF signal is being received and is 'non-conducting' otherwise. Similarly, the controller may control the bias voltage so that the conduction state of each semiconductor device is 'conducting' when controller determines that an RF signal above a certain power threshold is being received and is 'non-conducting' otherwise. Alternatively, the controller may control the bias voltage so that the conduction state of each semiconductor device is 'non-conducting' when the controller determines that an RF signal is being received and is 'conducting' otherwise. Similarly, the controller may control the bias voltage so that the conduction state of each semiconductor device is 'non-conducting' when the controller determines that an RF signal above a certain power threshold is being received and is 'conducting' otherwise. Many other criteria are possible for modifying a bias voltage of each semiconductor device in response to receiving the RF signal.

The controller may comprise a receiving element, such as an antenna or inductor, arranged to receive the RF signal. The controller may further comprise a converter arranged to convert the RF signal into a clock signal to modify the bias voltage of each semiconductor device when the device receives the RF signal. The converter may comprise a comparator to digitalise the RF signal, i.e. change the analogue RF signal into a digital signal. The converter may further a frequency divider to decrease the frequency of the RF signal and a multivibrator to further decrease the frequency of the RF signal to a specific frequency. The specific frequency may be determined by an RC circuit.

One or more of the plurality of semiconductor devices may be a transistor, diode or a varactor and the controller may comprise a variable DC voltage supplier arranged to control the bias voltage of the transistor or varactor to tune the resonant frequency of the array. Hence the variable DC voltage supplier can determine the conduction state of the semiconductor device if the semiconductor device is forward biased or can determine the capacitance of the semiconductor device if the semiconductor device is reverse biased. The variable DC voltage supplier may be a potentiometer arranged to receive a DC voltage from a DC voltage power supply and arranged to supply a variable DC voltage to the transistor or the varactor.

Each semiconductor device of the plurality of semiconductor devices may be a MOSFET or a diode. All semiconductor devices may be of the same type, or the semiconductor devices may be different to other semiconductor devices in the plurality of semiconductor devices.

The plurality of conductive elements may be supported by a dielectric material. The dielectric material can hold the conductive elements so that the conductive elements do not move (in position or orientation) with respect to each other. For example, the conductive elements may be embedded in the dielectric material or fixed onto a surface of the dielectric material.

Each conductive element may be made from a non-magnetic metal. For example, a non-magnetic metal may be adequately non-magnetic if it is safe to place in a magnetic field of more than 1 Telsa, up to 3 Tesla, or even 7 Tesla. For example, metallic materials comprising substantial amounts of Iron or Nickel are typically unsuitable whereas copper, brass, silver, etc. are suitable.

In another aspect of the disclosure an MR system comprises an imaging region arranged to receive an object to be imaged and a magnetic field generator arranged to produce a static magnetic field in the imaging region. The static magnetic field to be produced may be a gradient magnetic field. The MR system further comprises an RF transmitter arranged to irradiate the object with an RF signal and an RF receiver arranged to receive a return RF signal from the object for imaging the object. The MR system further comprises the device for concentrating the magnetic field of RF signals in the MR system as described above. The device may have a resonating frequency matching an RF frequency of the RF signal and the RF signal has a wavelength greater than a respective dimension of each conductive element. The device is arranged between the imaging region and either the RF transmitter or the RF receiver, or both. In this way the device can redistribute energy between electric and magnetic fields in the imaging region receiving the RF signal. Accordingly, the device may locally increase the magnetic field of the RF signal over all or part of the imaging region where the object to be imaged will be located. Alternatively or additionally, the device may increase the magnetic field of the return RF signal at the RF receiver.

The system may further comprise a transmitter controller, arranged to control the RF transmitter. The transmitter controller may control the frequency, pulse duration or power of the RF signal, or any other parameter determined by the RF transmitter. The controller of the device, which is arranged to control the bias voltage of each semiconductor device in the device, may be arranged to receive control signals from the transmitter controller to change the bias voltage of the plurality of semiconductor devices in coordination with transmission of the RF signal. For example, the controller may control the semiconductor devices to be 'conducting' when the control signal indicates RF signals are being transmitted, and 'non-conducting' when the RF signal is not being transmitted, or vice versa. The controller may receive control signals from the transmitter controller wirelessly.

In another aspect of the disclosure, a method of concentrating the magnetic field of a RF signal in an object to be imaged in an MR system comprises placing a device, comprising a plurality of conductive elements arranged in an array, in proximity of the object to be imaged using the MR system. The array is arranged to redistribute energy between electric and magnetic fields of RF radiation at a resonant RF frequency when receiving the RF signal having a RF wavelength greater than a respective dimension of each conductive element. The conductive elements and array may be as described above with reference to the device for concentrating the magnetic field of RF signals in the MR system. The method comprises irradiating the conductive elements and the object with the RF signal. The RF signal causes a return RF signal to be generated by the object and the method comprises receiving the return signal to image the object. The method further comprises controlling a bias voltage of a plurality of semiconductor devices connected to conductive elements in the array to change the resonant frequency of the plurality of conductive elements.

The controlling of the bias voltages of the plurality of semiconductor devices may be so as to not concentrate the magnetic field of the RF signal when irradiating the conductive elements and object with the RF signal (also referred to as the 'transmit' signal). The controlling is may also be so as to concentrate the magnetic field of the RF signal when receiving the return RF signal from the conductive elements and the object to image the object. Alternatively, the controlling of the bias voltage of the plurality of semiconductor devices may be so as to not concentrate a magnetic field of the return RF signal when receiving the return RF signal from the conductive elements and object to image the object and be so as to concentrate the magnetic field of the RF signal when irradiating the conductive elements and object with the RF signal.

The controlling of the bias voltages of the plurality of semiconductor devices may be to tune the resonant frequency of device to the RF signal frequency. For example, the resonant frequency may be tuned to the RF signal in response to the permittivity and/or permeability of the object modifying the RF signal frequency.

The device in the above methods may be any of the devices as described above.

BRIEF DESCRIPTION OF THE FIGURES

Specific embodiments are now described by way of example and with reference to the accompanying drawings, in which.

DETAILED DESCRIPTION

In overview, the present disclosure relates to a tunable device arranged to redistribute RF fields and enhance the magnetic field of incoming RF signal into certain areas, such as areas near a patient under diagnosis in an MRI system. The resonant frequency at which device enhances RF magnetic field can be tuned to or from a frequency of the incoming RF signal so that the device selectively operates at only advantageous times during the MRI RF signal sequence.

Introduction to MRI Field Concentrator Devices

Figure 1:
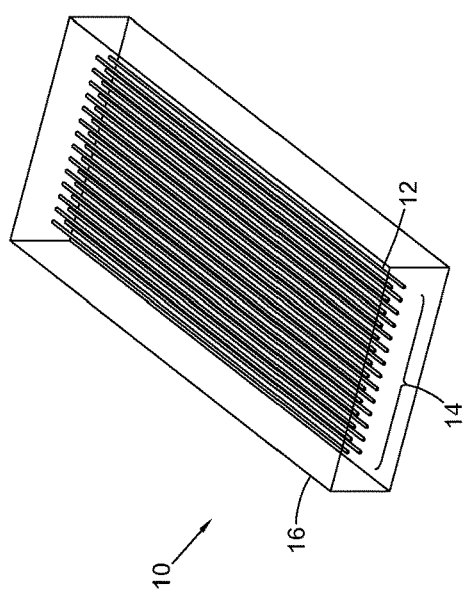
FIG. 1 shows an isometric view of a device for concentrating magnetic field of RF signals in an MR system.

With reference to FIG. 1, a device 10 suitable for concentrating the magnetic field of RF signals in an MRI system comprises a plurality of wires 12 arranged in an array 14. The wires 12 are supported by a dielectric layer 16. The wires are elongate conductive elements, having a length in a first direction much longer than the width and height dimensions. The wires are made from a non-magnetic or non-ferrous metal. The longitudinal axes of the wires 12 are substantially parallel.

The wires 12 are arranged in a two-dimensional periodic array 14, having the wires 12 evenly spaced apart in two dimensions along the height and width of the device 10. As shown in FIG. 1, the array 14 comprises two rows of fourteen wires 12. The array 14 of wires 12 is embedded in the dielectric layer 16, which supports the wires 12 in the array and positions each wire 12 with respect to each other.

The array 14 and wires 12 of the array are arranged such that, when an RF signal is incident on the array 14, wires modify the RF electric and magnetic field in the vicinity of the midpoint along the length of each wire 12.

To produce the field redistribution phenomenon, the length of each wire is selected to meet the Fabry-Perot condition for the first eigenmode at the operating frequency of an MRI system. This condition is also known as half-wavelength resonance, since the length corresponds to approximately half of the wavelength in the medium of the operating frequency. For example, for 1.5 T MRI machine the operating frequency is equal to 63.8 MHz. The length of wires 12 of the device 10 can be selected using the following equation:

$$f = \frac{c}{2L\sqrt{\varepsilon}} \quad (1)$$

where $\varepsilon$ is the permittivity of the environment that the wires are in, L is the length of each wire, c is the speed of light, and f is frequency. The permittivity of the environment of the wires is affected primarily by the permittivity of the material in which the wires are embedded, although other nearby materials may also affect this value. For a frequency of 63.8 MHz in a medium with dielectric constant 81, this corresponds to a wire length of 26.1 cm. Note that this is less than the wavelength corresponding to the operating frequency, i.e. the frequency of the RF signal for which the device is arranged to concentrate the magnetic field. Since the elements are elongate, the width and height are therefore also subwavelength. Instead of using equation 1, the appropriate length for a given frequency can be determined by experimentation or simulation.

In accordance with the present disclosure, for the first Fabry-Perot mode, the largest magnetic field is localized in the middle part of the surface of the device 10 and the electric field is localized near the edges of the wires 12. The first Fabry-Perot mode is modified due to the nearfield mutual coupling between wires, but the mode structure of an array is very close to the mode structure of the single wire for the half wavelength resonance frequency. In particular, there is a maximum of the magnetic field near the centre and the maxima of the electric field are localized near the ends of wires 12.

A device as described above can be used in Magnetic Resonance (MR) systems (including MRI systems and Magnetic Resonance Spectroscopy (MRS) systems) to improve the RF signal for imaging an object. This is because an increased magnetic field in the region of the object to be imaged increases the SNR and decreasing the electric field in the region reduces the SAR. The specific embodiments disclosed herein are described primarily in context of MRI systems, but are likewise applicable to MRS systems.

The arrangement described above with reference to FIG. 1 is one particular example of a device for redistributing the magnetic and electric fields. However, there are many variants of this device which work in an equivalent manner. For example, conductive elements other than wires are possible such as split ring, loops, swiss rolls or curved wires. Likewise, although circular cross-section wires are shown, other cross-sectional shapes behave in an equivalent manner. In alternative arrangements, instead of being periodic the array may be aperiodic, i.e. have irregular spacings between the conductive elements. Furthermore, rather than a two-dimensional array as shown in FIG. 1, the array may be one-dimensional or three-dimensional. The array may comprise as many or as few individual conducting elements as required to produce the phenomenon of redistribution of fields, as required in the particular application for which it is designed.

Although the above description of the phenomenon of field redistribution by the device 10 is described according to half-wavelength resonance corresponding to the first Fabry-Perot mode, the disclosed arrangements for tuning and detuning a device for concentrating the magnetic field of RF signals in an MRI system apply to any mechanism of field redistribution. For example, other arrays of conductive elements may focus or steer incoming radiation at a particular operating frequency. Collections of subwavelength conductive elements arranged in an array to perform a particular manipulation on incoming radiation are known generally as metamaterials. The principles disclosed herein are applicable to any metamaterials used for concentrating the magnetic field of an RF signal in an MR system.

Tunable Device for Concentrating the Magnetic Field of an RF Signal

To change the resonant frequency of the device 10, or other devices for concentrating the magnetic field of RF signals in an MRI system, the device 10 is provided with an arrangement as will now be described with reference to FIG. 2.

Figure 2:
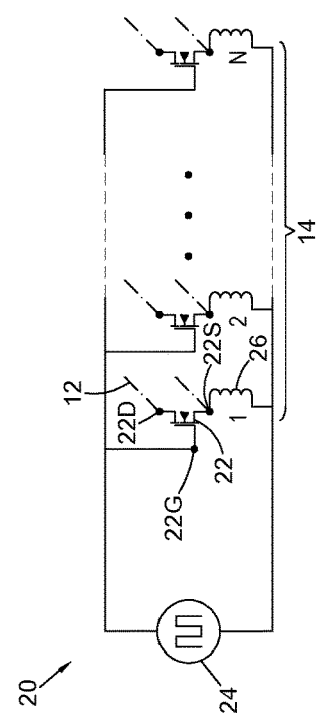
FIG. 2 shows a switch circuit for a device of FIG. 1.

With reference to FIG. 2, the device 10 comprises a switch circuit 20. The switch circuit 20 includes a plurality of transistors 22 connecting the wires 12. Each transistor 22 connects between a pair of adjacent wires 12 with its source 22S connected to one wire of the pair and its drain 22D connected to the other wire of the pair. For example, in an array having two rows of conductive elements as described with reference to FIG. 1, each respective transistor 22 is connected between adjacent wires 12 in the same row. FIG.

2 is a schematic and does not show all of the transistors, labelling the first connected wire pair '1' and the second connected wire pair '2', where there is a total of N connected wire pairs in the array 14. In other arrangements, each wire 12 may be connected to other wires 12 via more than one transistor, e.g. so that all the wires 12 are electronically connected to each other via the transistors.

A clock signal 24 generated by a control circuit is applied to gate 22G of each transistor 22 and the source 22S of each transistor 22 via a respective inductor 26. The clock signal determines the gate voltage of each transistor 22 and hence the conductivity of the source-drain connection the transistor. When the clock signal 24 is on, each transistor will conduct between its source and drain, thereby shorting the adjacent wires 12 in each connected pair and changing the resonant frequency of the device. The inductors 26 are included, for example, to isolate the transistor sources 22S and wires 12 from each other at the operating frequency by having a high impedance at operating frequency (such as 63.8 MHz) but having a low impedance for DC voltages to allow biasing. Hence the inductances of the inductors are large enough to isolate the wires at the operating frequency while small enough to activate the transistors by a single clock supply with a frequency on the order of tens of kHz. An exemplary inductance of each inductor is 3.3 pH Each transistor is forward biased by applying the higher potential of the clock signal 24 to the gate compared to the potential applied to the source. When the gate voltage crosses a threshold voltage (Vth), the transistor produces a very small impedance between drain and source; whereas, below the threshold voltage, the transistor has a high impedance between drain and source. The transistors 22 may each be a MOSFET (Metal-Oxide-Semiconductor Field-Effect-Transistor), or any other kind of transistor. Similarly, instead of a transistor, any semiconductor device which has a conduction state that can be controlled by a bias voltage electronically can be used, e.g. a diode. By applying a potential between the anode and cathode, using the clock signal 24, the conduction state of the diode can be controlled.

The switch circuit 20 may be supported in or on the dielectric material 16 of device 10. Alternatively, part of the switch circuit 20 such as the transistors 22 are supported by the dielectric material and can be connected to the clock signal via one or more electronic contacts.

Figure 3:
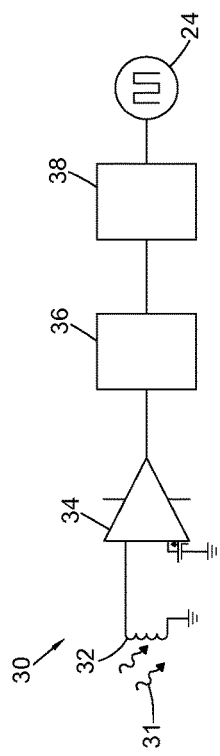
FIG. 3 shows a control circuit for a device of FIG. 1.

With reference to FIG. 3, in a first arrangement the clock signal 24 is produced using a control circuit 30 which receives an RF signal 31 and converts the RF signal 31 into the clock signal 24. The control circuit 30 has an inductor 32 to receive the RF signal which is electrically connected to an input of a comparator 34. The comparator 34 converts the small sine wave received by the inductor 32 to a rail-to-rail square wave, i.e. converts the analogue signal into a digital signal, by comparing to a reference voltage. The comparator has a response time fast enough to convert the RF signal equal to or faster than the operating frequency of an MRI system it is designed for, i.e. the Larmor frequency. The output of the comparator 34 is electrically connected to the input of a frequency divider 36 arranged to convert the digitalised RF signal to a lower frequency. A suitable frequency divider 36 for an RF signal 31 of approximately 64 MHz is an asynchronous counter (8-12 bit) which converts the digitalised RF signal 31 into an intermediate signal with a frequency having a magnitude of tens or hundreds of kHz. The output of the frequency divider 36 is electrically connected to a multivibrator 38 arranged to further down-convert the signal from the frequency divider 36 to a particular set frequency determined by an RC time constant of the multivibrator 36. A suitable multivibrator 38 is a monostable multivibrator with a fixed output frequency in the range 1 to 10 kHz and a duty cycle of greater than 80%. In other words, while the monostable multivibrator 38 receives an input signal, the monostable multivibrator 38 output has a relatively high (ON) voltage for more than 80% of time and a relatively low (OFF) voltage for the rest of the cycle. The time period of one cycle, e.g. the time between rising edges of the output, is given by one divided by the fixed output frequency. The value of the duty cycle is determined by an RC circuit which characterises the multivibrator. The output of the multivibrator 38 is a clock signal 24 to be supplied to the switch circuit as described above.

The arrangement described above with reference to FIG. 3 is an example of a control circuit 30. However different and/or additional components may be included to produce the clock signal 24 from the RF signal 31. For example, instead of an inductor 32, an antenna or other receiving element may be used. Likewise, there are components other than a comparator 34, a frequency divider 36 and a multivibrator 38 which can provide a circuit which converts an analogue RF signal 31 into a digital clock signal with a lower frequency. Alternatively, a control circuit which does not convert the RF signal into a digital signal may be used, e.g. by maintaining an analogue signal and two transistors, one for each half cycle of the analogue signal. Alternatively, a control circuit may not need to convert the RF signal into a low frequency, depending on how different the frequency of the RF signal is compared to the frequencies at which the circuit components can operate.

Figure 4:
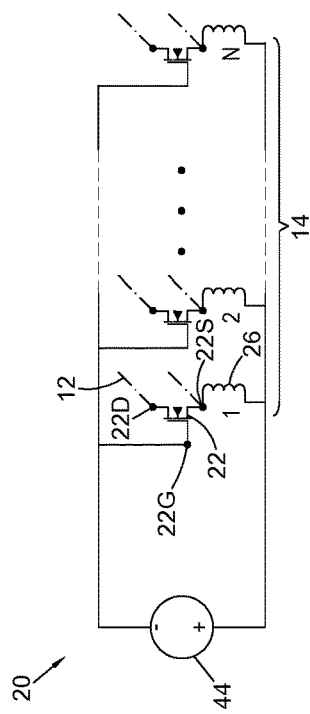
FIG. 4 shows a switch circuit for a device of FIG. 1.

With reference to FIG. 4, in a second arrangement a potentiometer 44 controls the signal which determines the bias voltage of the transistors 22. This in turn determines the capacitance of the transistors between conductive elements and the resonance frequency of the array 14. Hence, instead of the control circuit 30 shown in FIG. 3, the potentiometer 44 acts as a controller for the switch circuit 20 as shown in FIG. 2. Apart from the inclusion of the potentiometer 44, the switch circuit 20 is as described for FIG. 2 and can have any of the variants thereof. One end of the potentiometer 44 is connected to each transistor gate 22G and the other end is connected to each transistor source 22S via an inductor 26. The higher potential end of the potentiometer 44 is applied to the source 22S of the transistors to reverse bias the transistors 22. A DC power is input to the potentiometer 44 so that the controlled resistance of the potentiometer 44 controls the gate voltages of the transistors 22. Hence the potentiometer 44 supplied with a DC power input acts as a variable DC voltage supplier. Alternative variable DC voltage suppliers may be used instead of the potentiometer 44. When the transistors are reverse biased, varying the gate voltage varies the bias voltage and therefore varies the capacitance between the drain and source of each transistor. This in turn varies the impedance, i.e. a conduction state, of the transistor to vary. Hence the potentiometer 44 controls the conduction state of the transistors as described above. Accordingly, controlling the resistance setting of the potentiometer 44 controls the capacitance between the wires 12 in array 14 of device 10, and therefore controls the resonant frequency of device 10. Consequently, varying the resistance setting of the potentiometer 44 will tune or de-tune the frequency at which the device 10 concentrates the magnetic field of RF signals in an MRI system. The potentiometer 44 can itself be controlled by a control circuit which receives an RF signal in the MRI system, thereby automatically tuning/de-tuning the device 10 depending on whether or not an RF signal is present or depending on the strength of the RF signal. Alternatively, the potentiometer 44 can be controlled using control signals from other components in the MRI system, either wirelessly or via electronic connection. For example, an MRI system may monitor the detuning of an RF receive coil and control the potentiometer 44 to tune the device 10 resonant frequency back to the Larmor frequency.

Figure 5:
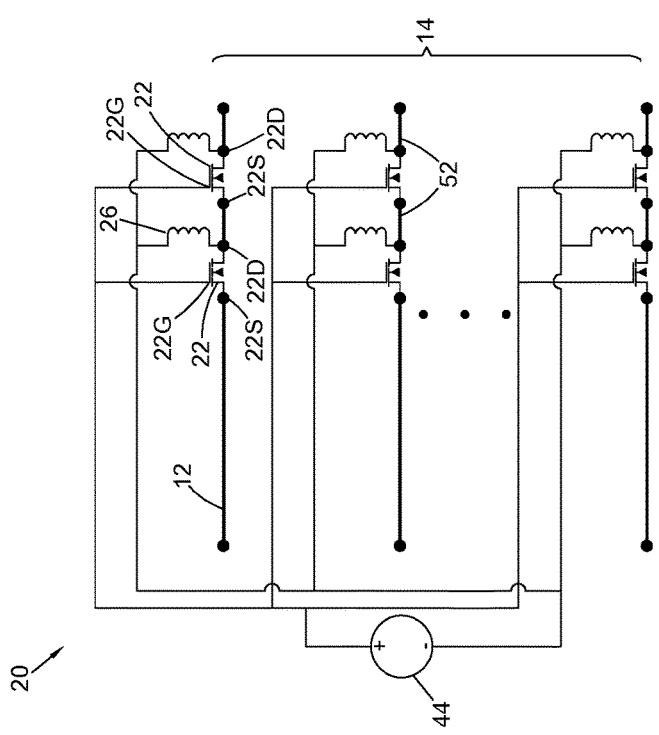
FIG. 5 shows a switch circuit for a device of FIG. 1.

The switch circuit 20 as described above uses shorting between wires 12 to change the resonant frequency of the array 14 of device 10. However, this can be achieved in other ways as well. With reference to FIG. 5, the array 14 of the same wires 12 comprises wire extensions 52. The wire extensions 52 are arranged parallel to the wires 12, with each respective wire having a wire extension 52 located at an end of the respective wire 12. The wire extensions 52 have the same longitudinal axis as the wires 12. As shown in FIG. 5, multiple wire extensions 52 are arranged in a line from the end of each wire 12. However, in some arrangements, there may only be a wire extension 52 per wire 12. The wire extensions 52 have the same width and height dimensions as the corresponding wires 12 and are made from the same material. However, the wire extensions 52 are shorter in length than the wires 12. For example, the wire extensions 52 may be one tenth of the length of the wires, although the ratio of lengths will depend on how large a tuning range the device requires. FIG. 5 is a schematic drawing for understanding this arrangement and the relative lengths of the wires 12 and wire extensions 52 are exemplary. Furthermore, FIG. 5 does not show all of the transistors in the device 10 connected to the array 14.

Each transistor 22 connects between a wire 12 and a corresponding first wire extension 52 with its source 22S connected to the wire 12 and its drain 22D connected to the corresponding first wire extension 52. Additional transistors connect between the first wire extensions 52 and second wire extensions 52 corresponding to the same wire 12, with a source 22S connected to the first wire extension 52 and its drain 22D connected to the corresponding second wire extension 52. Accordingly, the wires 12 are connected to wire extensions 52 by a respective transistor 22. However, each wire 12 and group of wire extensions 52 are isolated from the other wires 12 and the corresponding wire extensions 52.

As previously described with reference to FIG. 2 for the switch circuit 20 arrangement, a clock signal 24 (from a control circuit 30 or from a DC source via a potentiometer 44) is applied to gate 22G of each transistor 22 and the source 22S of each transistor 22 via a respective inductor 26. The clock signal determines the gate voltage of each transistor 22 and hence the conductivity of the source-drain connection the transistor. When the clock signal 24 is on, each transistor will conduct between its source and drain, thereby shorting each wire 12 and the corresponding wire extensions 52 in each group. This changes the effective length of the wires 12 to be the length of the wire 12 plus the length of each wire extension 52 it is connected to. Since the resonant frequency of the device 10 depends on the effective length of the wires 12, this change shifts the resonant frequency of the device 10. For example, the wires 12 may have a length given by equation 1, approximately half the wavelength for a frequency of 63.8 MHz, but when the transistors are conducting the change in effective length shifts the resonant wavelength by approximately 5 MHz. The amount that the resonant frequency shifts by may depend on a number of different parameters, such as properties of the transistor, length of the wires and the environment that the wires are in. Accordingly, the clock signal controls which frequency the device will redistribute energy between electric and magnetic fields of RF radiation and can tune/de-tune this to/from the operating frequency of an MRI system.

The switch circuit 20 described with reference to FIG. 5 can have any of the variants as described above with reference to FIGS. 1-4, e.g. any type of transistor or other semiconductor device having an adjustable conduction state or capacitance determined by a bias voltage. Likewise the switch circuit 20 described with reference to FIG. 5 can have any type of clock signal, number of wires 12 etc.

Figure 6A:
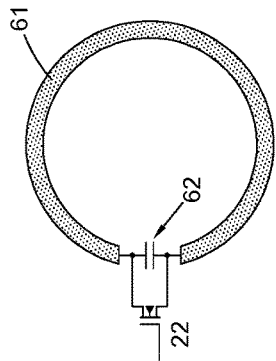
FIG. 6A to 6C show three alternative shapes of conducting elements.
Figure 6B:
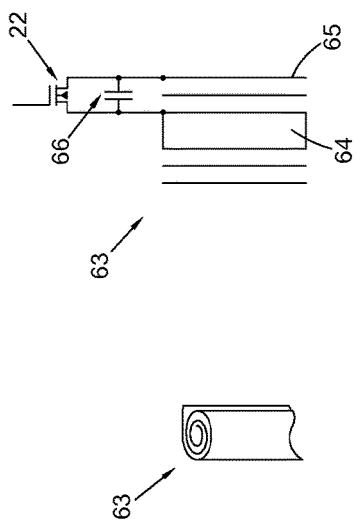
Figure 6C:
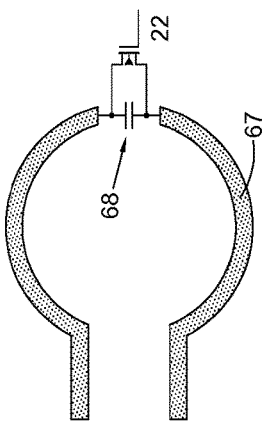

With reference to FIG. 6, the devices, systems and methods described herein apply to arrays of conductive elements other than wires 12 as described with reference to FIGS. 1-5. With reference to FIG. 6A to 6C, instead of an array of wires 12, in some arrangements the device for concentrating a magnetic field of RF signals comprises an array of split rings 61, an array of swiss rolls 63, or an array of split loops 67. A switch circuit 20 as described with reference to FIG. 2 can be used for an array of split rings, swiss rolls or split loops in the same manner as for wires 11 or other conducting elements.

With reference to FIG. 6A, each split ring 61 has a split-ring capacitor 62 electrically connected across two ends of the split ring 61, i.e. across the 'split'. A transistor 22 is connected to each side of the split-ring capacitor 62, wherein the bias voltage of the transistor 22 controls the resonant frequency of the split ring 61.

With reference to FIG. 6B, a swiss roll 63 comprises a mandrel 64 with a conductive winding 65 wrapped around the mandrel 64. The winding 65 forms multiple layers wrapped around the mandrel 64. A swiss-roll capacitor 66 is connected between the mandrel and an outer layer of the winding 65. A transistor 22 is connected to either side of the swiss-roll capacitor 66, wherein the bias voltage of the transistor 22 controls the resonant frequency of the swiss roll 63.

With reference to FIG. 6C, a split loop 67 comprises an incomplete loop which has a 'split' between two portions of the incomplete loop. The split loop 67 has a split-loop capacitor 68 electrically connected across the two portions of the split loop 67, i.e. across the 'split'. A transistor 22 is connected to each side of the split-loop capacitor 68, wherein the bias voltage of the transistor 22 controls the resonant frequency of the split loop 67. Alternatively, the array of conducting elements may comprise curved wires, which are otherwise arranged according to the wires 12 as described with reference to FIG. 1, except that the wires are curved.

In the arrangements having alternative conducting element shapes, i.e. split ring 61, swiss roll 63, split loop 67 and curved wire arrangements, the transistors are incorporated into the control circuit 20 as described above reference to FIGS. 2-4. Likewise, they can be controlled by a control circuit 30 as described above with reference to FIG. 3, or by a potentiometer 44 as described above with reference to FIG. 4 or 5. Since the gate voltage and/or bias voltage of each transistor 22 in the array 14 of conducting elements controls the resonant frequency of the respective conducting element, corresponding methods can be used to tune or de-tune the resonant frequency of a device comprising conducting elements having any of the shapes described herein. The techniques described herein can also be applied to additional conducting elements shapes.

MRI System

Figure 7:
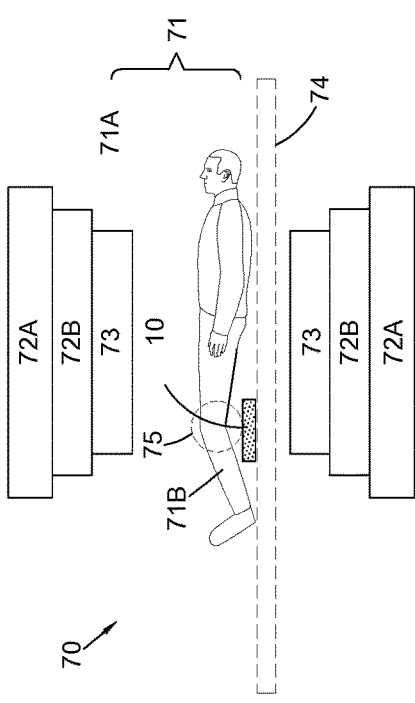
FIG. 7 shows a Magnetic Resonance system.

An MRI system comprising the device 10 as described above will now be described with reference to FIG. 7.

An MRI system 70 comprises an imaging region 71 arranged to receive an object to be imaged, e.g. a human body 71A or human limb 71B. A first coil 72A produces a static magnetic field in the imaging region 71 and, in operation, a gradient coil 72B produces a gradient to static magnetic field in the imaging region. Together, the first coil 72A and gradient coil 72B are a magnetic field generator 72. The system further comprises an RF transmit coil 73 for irradiating the object with an RF signal 31 (not shown). The RF transmit coil 73 is arranged to transmit RF signals as a pulse and then have a delay between pulses during which the return RF signal is received. A table 74 is located in the imaging region 71 to support the object to be imaged. The device 10 for concentrating the magnetic field of RF signals in the MRI system 70 as described above is located in the imaging region 71 in proximity of the object, or a particular target region 75 of the object to be imaged. The device is arranged to concentrate the magnetic field of RF signals in the object to imaged. The device is arranged between the RF transmit coil 73 and object so, if tuned to the RF signal frequency, the device 10 concentrates the magnetic field of the RF signal from the RF transmit coil 73 to the object in the target region 75, thereby improving the SNR. As described above, this is by redistributing the energy between electric and magnetic fields of the RF signal, increasing the magnetic field in the target region 75 and reducing the electric field in the target region 75 which reduces the SAR.

The RF transmit coil 73 may also function as an RF receiver, with the return signal from the object being recorded to image the object. Alternatively, the table 74 may comprise a dedicated coil 76 (not shown) which functions as an RF receiver as it receives the return signal in order to image the object. In either arrangement, when the device is positioned between the object and the RF receiver (tuned to the RF signal), the device 10 will also concentrating the magnetic field of the return signal as it passes from the object to the RF receiver.

The device 10 may be fixed on, or embedded in, the table 74 or may be a mat which is laid on the table 74 prior to introducing the object to be imaged into the imaging region. Alternatively, the device may be placed on the object, e.g. in an item of clothing worn by a patient.

As described further below, the tuning/de-tuning provided by the switch circuit 30 allows for the device to selectively concentrate the magnetic field of either the transmitted RF signal or the return signal, but not the other.

Figure 8:
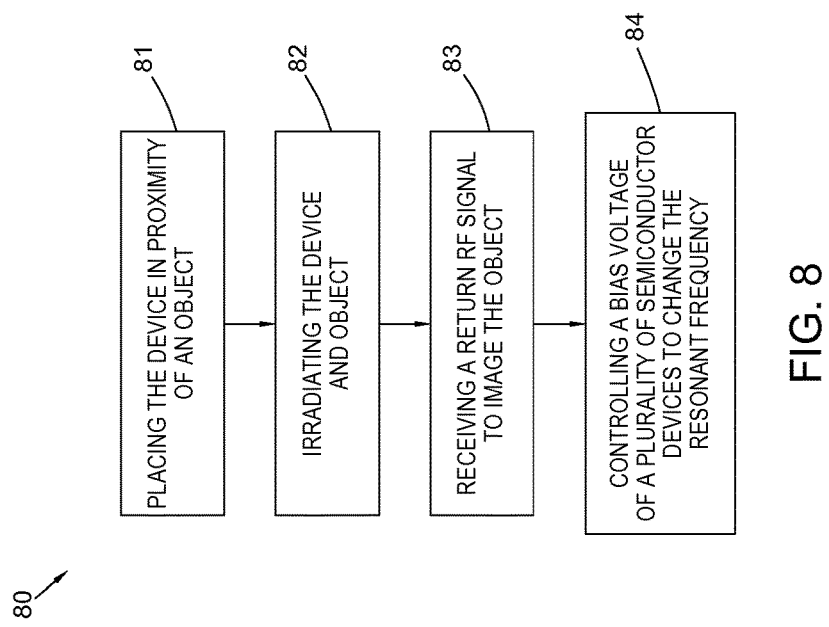
FIG. 8 shows a method of concentrating a magnetic field of an RF signal in an object to be imaged in an MR system.

Method of Controlling a Device for Concentrating the Magnetic Field of an RF Signal With reference to FIG. 8, a method 80 of concentrating the magnetic field of an RF signal in an object to be imaged in the MRI system described above comprises placing 81 the device 10 in proximity of an object to be imaged using the MRI system 70. The device 10 and MRI system 70 are as described above with reference to FIGS. 1 to 7. The resonant frequency of the device 10 is chosen to approximately match the operating frequency of the MRI system. Placing the device 10 in proximity of the object to be imaged may involve laying the device 10 on a table 74 in the imaging region 71 on the MRI system 70. Alternatively, the device may be already in the MRI system and placing the device in proximity of the object entails bringing the object to be imaged into the MRI system and into proximity of the device 10. As an example, with reference to FIG. 7, the device 10 is placed on the table 74 outside the imaging region 71 of the MRI system at a location where a knee of the human body 71A (i.e. the patient) to be imaged will be located. The patient then is positioned on the table 74 with the knee to be imaged over the device 10 and the table 74, along with the patient and device 10, is positioned into the imaging region 71 prior to commencing the imaging process. Other examples of body parts the MRI system can be used to image include a wrist, a spine, etc. or indeed the MRI system can image an entire body. For the MRI process to begin, a static magnetic field is produced in the imaging region, optionally having a gradient field according to known MRI techniques.

The method 80 comprises irradiating 82 the device and object with an RF signal from the RF transmit coil 73 and receiving 83 a return RF signal from the object to image the object. The irradiating comprises transmitting an RF signal as an RF pulse. The RF signal pulse travels to a target region 75 of the object to be imaged via the device 10. If the device is tuned to the frequency of the RF signal pulse, the device concentrates the RF signal in the target region 75 by increasing the magnetic field and reducing the electric field. After impinging on the target region 75, the RF signal pulse is emitted from the target region 75 as a return RF signal. The return RF signal passes through the device 10 again on return to the RF transmit coil 73 for detection and imaging of the target region 75. If the device is still tuned to the frequency of the return RF signal, the device concentrates the RF signal by increasing the magnetic field and reducing the electric field from the target region 75.

The method comprises controlling 84 a bias voltage of a plurality of transistors 22 connected to the wires 12 in the array 14 to change the resonant frequency of the plurality of wires 12. For example, the resonant frequency may be changed to be substantially equal to the RF signal during a one period of the MRI transmission/receiving sequence and changing again to be substantially different to the RF signal during another period of the MRI transmission/receiving sequence.

According to a first alternative, the tunable device 10 as described herein is controlled such that the resonant frequency of the device 10 is de-tuned from the frequency of the RF signal 31 during transmission of the RF signal by the RF transmit coil 73. The resonant frequency of the device is then tuned to the frequency of the return RF signal during receiving of the RF signal from the object to be imaged. This is performed by a device as described with reference to FIGS. 2 and 3, wherein the switch circuit 20 is controlled by the control circuit 30 having an inductor 32 to receive the RF signal 31. When the RF signal 31 is received by the inductor 32 during the transmission of the RF signal by the RF transmit coil 73, this is converted by the converter 34, 36, 38 into the clock signal 24 which raises the gate voltage 22G, shorting wires 22. Hence the resonant frequency is adjusted away from the normal operating frequency and the wires 12 of device 10 do not perform the redistribution of energy between magnetic and electric fields. An advantage of this detuning of the device 10 in the transmission period of the MRI system is that it avoids creating undesirably high fields in the object to be imaged. Accordingly, a higher magnetic field MRI system can be used without endangering the object with high fields. For example, detuning the device during RF transmission reduces the SAR in the object to be imaged because the electric field in the target region 75 of the object is reduced.

When the transmission of the RF signal 31 pulse is finished, the inductor ceases to pick up the signal and the digital signal does not generate the clock signal 24. Hence the transistor 22 gate voltage drops to zero (i.e. the bias voltage decreases), electrically isolating the wires 12. This means that resonant frequency of the device 10 is tuned back to the operating frequency of the MRI system. Hence, when the object emits the RF signal as a return RF pulse, the device performs the amplification of the signal as described above, thereby improving the SNR. Further, since a high magnetic field MRI system can be used due to the automatic detuning during the transmission period, the return RF signal is of higher quality even before the SNR is improved by concentrating the magnetic field of device 10. Hence the device and methods as disclosed herein improve the image quality of MRI or allow for the same quality images to be performed in a shorted period of time.

A further point to note is that the return RF signal itself does not trigger the switch circuit 20 to short the wires 12 since the return RF signal is of too lower power to create a clock signal capable of raising the transistor 22 gate voltage enough to short the wires. The threshold at which a signal triggers the clock signal can be set using the reference voltage of the comparator 34 as described with reference to FIG. 3. If the received signal has a low voltage such that the comparator input never exceeds the reference voltage, then the comparator output will always be zero and no clock signal generated.

Another way of performing the first alternative, wherein the tunable device 10 is de-tuned during RF signal transmission and is re-tuned for the return RF signal from the object, is using wire extensions 52 as described above with reference to FIG. 5 and the control circuit as described with reference to FIG. 4. When the inductor 32 receives the RF signal 31, the transistor gate voltage is raised by the clock signal 24 and the effective length of each wire 12 increases due to connection with the wire extensions 52. Therefore, in the pulse transmission period, the resonant frequency of the device is de-tuned from the operating frequency of the MRI system and the device does not concentrate the magnetic field of the RF pulse in the object to be imaged. Similar to as described above, when the transmitted RF signal pulse ceases, the effective length of the wires 12 returns to approximately half of the wavelength corresponding to the MRI system operating frequency, i.e. meets the resonance frequency criterion for the return RF signal. Hence, the device is re-tuned to concentrate the magnetic field of the return RF signal.

Another way of performing the first alternative, wherein the tunable device 10 is de-tuned during RF signal transmission and is re-tuned for the return RF signal from the object, is using a potentiometer 44 as a controller as described with reference to FIG. 4. The potentiometer 44 can tune and de-tune the resonant frequency freely and so the exact timing and extent of the tuning can be determined by the input to the potentiometer. This can either be using a passive control circuit as described by FIG. 3 or using control signals from a controller of the MRI system. For example, control signals can be sent from a RF coil transmitter controller to coordinate the timing of RF signal transmission and de-tuning of the device 10, re-tuning the device for the return RF signal. Hence this provides an active way of protecting the object against high fields amplified by the device 10, while still taking advantage of the amplification of the device 10 during receiving the return RF signal from the object to be imaged.

According to a second alternative, the tunable device 10 as described herein is controlled such that the resonant frequency of the device 10 is tuned at the frequency of the RF signal 31 during transmission of the RF signal by the RF transmit coil 73. The resonant frequency of the device is then de-tuned from the frequency of the return RF signal during receiving of the RF signal from the object to be imaged. This can be performed by a device as described with reference to FIGS. 2 and 3, wherein the switch circuit 20 is controlled by the control circuit 30 having an inductor 32 to receive the RF signal 31.

However, to swap the periods which are tuned and de-tuned, the control circuit is configured inversely so that the clock signal is generated when no RF signal is received and vice versa. This can be done by using a reference clock signal as a first input to a two-input-one-output (2:1) multiplexer, configured such that for a second input logic of '0' the multiplexer output is the reference clock signal and for a second input logic '1' the output is zero. The second input selection logic is generated by a re-triggerable monostable multivibrator, such as according to the control circuit 30 described above with reference to FIG. 3. Alternatively the second input can be controlled by a signal from a microcontroller, wherein in the signal comprises a pulse with certain duration and duty cycle when there is an RF signal transmitted by the transmitter coil and zero when there is no RF signal received from the transmitter coil. In this inverted control circuit 30, when the RF signal 31 is received by the inductor 32 during the transmission of the RF signal by the RF transmit coil 73, no clock signal 24 is sent to the switch circuit 20.

However, when the RF signal is finished, a clock signal (e.g. the reference clock signal) is sent to the switch circuit which raises the gate voltage 22G, increasing the bias voltage and shorting the wires 22. Hence the resonant frequency shifts away from the normal operating frequency and the device 10 wires 12 do not perform the redistribution of energy between magnetic and electric fields for the return signal. An advantage of this detuning of the device 10 in the return period of the MRI system is that, if a dedicated receive coil is used, this receive coil may not be optimized by the concentration phenomenon of the device. In this case, the dedicated receive coil would perform better without the concentration of the magnetic field of the RF signal. Accordingly, de-tuning the device during for the return signal improves the performance of the receive coil.

Another way of performing the second alternative, wherein the tunable device 10 is tuned to the RF signal frequency during RF signal transmission and is de-tuned for the return RF signal from the object, is using wire extensions 52 as described above with reference to FIG. 5 and the control circuit as described with reference to FIG. 4. For example, the effective length of the wires 12 plus wire extensions 52 can be set to meet the resonance condition for the RF signal frequency, whereas the wires 12 alone do not. When the inductor 32 receives the RF signal 31, the transistor gate voltage is raised by the clock signal 24 and the effective length of each wire 12 extends due to connection with the wire extensions 52. Therefore, in the pulse transmission period, the resonant frequency of the device is tuned to the operating frequency of the MRI system and the device concentrated the magnetic field of the RF pulse in the object. Similar to as described above, when the transmitted RF signal pulse ceases, the effective length of the wires 12 returns to below half of the wavelength corresponding to the MRI system operating frequency, i.e. no longer meets the resonance frequency criterion for the return RF signal. Hence, the device is de-tuned so as not to concentrate the magnetic field of the return RF signal. As another example, instead of selecting new lengths of wire 12 and extensions, the inversely configured control circuit as described above can be used to swap the tuning/de-tuning periods.

Another way of performing the second alternative, wherein the tunable device 10 is tuned to the RF signal frequency during RF signal transmission and is de-tuned for the return RF signal from the object, is using a potentiometer 44 to control the clock signal 24 as described with reference to FIG. 4. The potentiometer can tune and de-tune the resonant frequency freely and so the exact timing and extent of the tuning can be determined by the input to the potentiometer. This can either be using a passive control circuit as described by FIG. 3 or using control signals from a controller of the MRI system. For example, control signals can be sent from a RF coil transmitter controller to coordinate the timing of RF signal transmission and tuning of the device 10, while de-tuning the device for the return RF signal. Hence this provides an active way of optimising a dedicated receive coil if the magnetic field concentration is a disadvantage for the receive coil.

According to a third alternative, the resonant frequency of the tunable device 10 can be controlled to maintain the resonant frequency substantially equal to the operating frequency of the MRI system RF signal. For example, one way this can be done is using a potentiometer 44 as described with reference to FIG. 2. The potentiometer 44 resistance can be controlled over a range of values. Accordingly, the DC source can provide a gate voltage to the transistors 22 having any variable value across a range of voltages. Variation in the gate voltage (and therefore also the bias voltage) will produce a variation in the capacitance of the transistors. This is because, when reversed-biased, a transistor capacitance depends on the bias voltage which can be controlled via the gate voltage. This in turn produces a range of resonant frequencies that the device 10 can be tuned to have. The continuous variable setting of the potentiometer 44 can therefore be translated into intermediate values of the resonant frequency, different to the resonant frequencies when the transistors are in either the 'conducting' or the 'non-conducting' state. This has the advantage of being able to match the resonant frequency of the device 10 to the operating frequency of the MRI system for a variety of objects to be imaged. Different objects, having different permittivities and/or permeabilities, will affect the operating frequency of the RF transmit coil 73 and the resonant frequency of the device 10. Hence being able to tune the resonant frequency of the device 10 over a range of values to match the operating frequency allows optimisation of the device 10 and MRI system.

Another way of performing the third alternative, i.e. tuning the resonant frequency across a range of values, is using the device 10 as described with reference to FIG. 5. To arrange the device 10 for variable tuning, multiple wire extensions 52 are arranged corresponding to each wire 12. A first transistor is arranged between each wire 12 and each first wire extension 52 and a second transistor is arranged between the first wire extension 52 and a second wire extension 52. Additional wire extensions and corresponding transistors can also be included to increase the range of resonant frequencies available. The gate voltages of the first transistor and the second transistor are controlled independently and sequentially to change the effective length of the wire 12. For example, each transistor or group of transistors may have an individual DC power supply between the gate and the source of the transistor. Alternatively each transistor or group of transistors may have a dedicated potentiometer to vary the gate voltage. If both the first and second transistors 22 are in a non-conducting conduction state, the wire 12 length determines the resonant frequency. If the first transistor is conducting but the second transistor is non-conducting, the wire 12 length plus the first wire extension determines the effective length and results in a different resonant frequency. If both transistors are conducting, then the total of the wire 12 and first and second wire extensions 52 is the effective length and results in a further different resonant frequency. With additional wire extensions and corresponding transistors, a larger range of resonant frequencies is available.

The invention claimed is:

1. A device for concentrating a magnetic field of RF signals in an MR system, the device comprising:
   a plurality of conductive elements arranged in an array, wherein the array is arranged to redistribute energy between electric and magnetic fields of RF radiation at a resonant RF frequency when receiving an RF signal having a RF wavelength greater than a respective dimension of each conductive element;
   a plurality of semiconductor devices each connected between two respective portions of the conductive elements; and
   a controller to control a bias voltage of each semiconductor device, thereby controlling the resonant frequency of the array.

2. The device as claimed in claim 1, wherein each of one or more of the plurality of semiconductor devices is coupled between a respective pair of the conductive elements, such that the conductive elements of the respective pair are shorted when the respective semiconductor device is conducting.

3. The device as claimed in claim 1, wherein the device comprises one or more conductive element extensions each arranged in line with a respective conductive element, and each of one or more of the plurality of semiconductor devices is coupled between a respective conductive element and a corresponding conductive element extension to extend an effective length of the respective conductive element when the respective semiconductor device is conducting.

4. The device as claimed in claim 1, wherein each conductive element is elongate and has a length of approximately half the wavelength of the resonant frequency, and the conductive elements are arranged substantially parallel to each other.

5. The device as claimed in claim 1, wherein the conductive elements comprise one or more curved elements, the one or more curved elements comprising one or more of a split ring, a loop, and a swiss roll, wherein a respective semiconductor device is coupled between ends of each of the one or more curved elements.

6. The device as claimed in claim 1, wherein the conductive elements comprise a curved wire medium, wherein a respective semiconductor device is coupled between one or more pairs of adjacent wires of the curved wire medium.

7. The device of claim 1, wherein the controller is arranged to modify the bias voltage of each semiconductor device in response to receiving the RF signal.

8. The device of claim 7, wherein the controller comprises:
   a receiving element arranged to receive the RF signal; and
   a converter arranged to convert the RF signal into a clock signal to change the bias voltage of each semiconductor device when the device receives the RF signal.

9. The device of claim 8, wherein the converter comprises:
   a comparator to digitalise the RF signal;
   a frequency divider to decrease the frequency of the RF signal; and
   a multivibrator to further decrease the frequency of the RF signal to a specific frequency.

10. The device of claim 1, wherein one or more of the plurality of semiconductor devices is a transistor or a varactor and the controller comprises a variable DC voltage supplier arranged to control the bias voltage of each transistor or varactor to change the resonant frequency of the array.

11. The device of claim 1, wherein each semiconductor device of the plurality of semiconductor devices is a MOSFET or a diode.

12. The device as claimed in claim 1, wherein the plurality of conductive elements is supported by a dielectric material.

13. The device as claimed in claim 1, wherein each conductive element is made from a non-magnetic metal.

14. An MR system comprising:
an imaging region arranged to receive an object to be imaged;
a magnetic field generator arranged to produce a static magnetic field in the imaging region;
an RF transmitter arranged to irradiate the object with an RF signal;
an RF receiver arranged to receive a return RF signal from the object for imaging the object; and
the device of any of claim 1 arranged between the imaging region and either the RF transmitter or the RF receiver, or both.

15. The MR system of claim 14, further comprising:
a transmitter controller;
wherein the controller of the device is arranged to receive control signals from the transmitter controller to change the bias voltages of the plurality of semiconductor devices in coordination with transmission of the RF signal.

16. A method of concentrating a magnetic field of an RF signal in an object to be imaged in an MR system, the method comprising:
placing a device comprising a plurality of conductive elements arranged in an array in proximity of the object to be imaged using the MR system, wherein the array is arranged to redistribute energy between electric and magnetic fields of RF radiation at a resonant RF frequency when receiving the RF signal having a RF wavelength greater than a respective dimension of each conductive element;
irradiating the device and object with the RF signal;
receiving a return RF signal from the conductive elements and object to image the object; and
controlling a bias voltage of each semiconductor device of a plurality of semiconductor devices connected to conductive elements in the array to change the resonant frequency of the plurality of conductive elements.

17. The method of claim 16, wherein the bias voltages of the plurality of semiconductor devices are controlled so as to not concentrate the magnetic field of the RF signal in the object when irradiating the conductive elements and the object with the RF signal and to concentrate the magnetic field of the return RF signal when receiving the return RF signal from the conductive elements and object.

18. The method of claim 16, wherein the bias voltages of the plurality of semiconductor devices are controlled so as to concentrate the magnetic field of the RF signal in the object when irradiating the conductive elements and the object with the RF signal and to not concentrate the magnetic field of the return RF signal when receiving the RF return signal from the conductive elements and object.

19. The method of claim 16, wherein the bias voltages of the plurality of semiconductor devices are controlled to tune the resonant frequency of device to the RF signal frequency.

20. The method as claimed in claim 16, wherein the device comprises
a plurality of conductive elements arranged in an array, wherein the array is arranged to redistribute energy between electric and magnetic fields of RF radiation at a resonant RF frequency when receiving an RF signal having a RF wavelength greater than a respective dimension of each conductive element;
a plurality of semiconductor devices each connected between two respective portions of the conductive elements; and
a controller to control a bias voltage of each semiconductor device, thereby controlling the resonant frequency of the array.

* * * * *

UNITED STATES PATENT AND TRADEMARK OFFICE
CERTIFICATE OF CORRECTION

| | |
|---|---|
| PATENT NO. | : 11,693,069 B2 |
| APPLICATION NO. | : 17/265384 |
| DATED | : July 4, 2023 |
| INVENTOR(S) | : Efthymios Kallos and Shimul Chandra Saha |

It is certified that error appears in the above-identified patent and that said Letters Patent is hereby corrected as shown below:

In the Claims

In Claim 14, Column 19, Line 24, delete "of any of" and insert -- of --.

Signed and Sealed this
Twenty-second Day of August, 2023

Katherine Kelly Vidal
*Director of the United States Patent and Trademark Office*